US008834837B2

(12) United States Patent
Kelson et al.

(10) Patent No.: US 8,834,837 B2
(45) Date of Patent: Sep. 16, 2014

(54) METHOD AND DEVICE FOR RADIOTHERAPY

(75) Inventors: Itzhak Kelson, Tel-Aviv (IL); Lior Arazi, Tel-Aviv (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 733 days.

(21) Appl. No.: 12/547,514

(22) Filed: Aug. 26, 2009

(65) Prior Publication Data

US 2009/0311173 A1 Dec. 17, 2009

Related U.S. Application Data

(62) Division of application No. 10/554,743, filed as application No. PCT/IL2004/000363 on Apr. 29, 2004.

(60) Provisional application No. 60/466,408, filed on Apr. 30, 2003.

(51) Int. Cl.
| | | |
|---|---|---|
| *A61K 51/00* | (2006.01) | |
| *A61M 36/14* | (2006.01) | |
| *A61K 51/12* | (2006.01) | |
| *A61K 36/14* | (2006.01) | |
| *A61N 5/10* | (2006.01) | |

(52) U.S. Cl.
CPC ............ *A61N 5/1007* (2013.01); *A61N 5/1001* (2013.01); *A61N 5/1027* (2013.01); *A61K 51/1282* (2013.01)
USPC ........................................ 424/1.11; 424/1.69

(58) Field of Classification Search
CPC combination set(s) only.
See application file for complete search history.

(56) References Cited

U.S. PATENT DOCUMENTS

| | | | |
|---|---|---|---|
| 3,754,999 A | 8/1973 | Merges | |
| 4,976,680 A | 12/1990 | Hayman et al. | |
| 5,342,283 A | 8/1994 | Good | |
| 5,713,828 A | 2/1998 | Coniglione | |
| 5,716,317 A | 2/1998 | Okano et al. | |
| 6,030,333 A | 2/2000 | Sioshansi et al. | |
| 6,059,714 A | 5/2000 | Armini et al. | |
| 6,060,036 A | 5/2000 | Armini | |
| 6,077,413 A | 6/2000 | Haefeli et al. | |
| 6,224,536 B1 | 5/2001 | Pike | |
| 6,475,644 B1* | 11/2002 | Hampikian et al. | 428/655 |
| 6,635,234 B1 | 10/2003 | Larsen et al. | |
| 6,666,811 B1 | 12/2003 | Good | |
| 6,709,693 B1 | 3/2004 | Dinkelborg et al. | |
| 6,723,052 B2 | 4/2004 | Mills | |
| 2002/0077520 A1 | 6/2002 | Segal et al. | |
| 2002/0131935 A1 | 9/2002 | Fisher et al. | |
| 2006/0039858 A1* | 2/2006 | Dadachova et al. | 424/1.49 |
| 2007/0041900 A1 | 2/2007 | Kelson et al. | |
| 2010/0062143 A1 | 3/2010 | Kelson et al. | |

FOREIGN PATENT DOCUMENTS

| | | |
|---|---|---|
| EP | 1191121 | 3/2002 |
| JP | 2001-509493 | 7/2001 |
| JP | 2001-520923 | 11/2001 |
| JP | 2002-143327 | 5/2002 |
| JP | 2002-534399 | 10/2002 |
| WO | WO 97/33628 | 9/1997 |
| WO | WO 99/02194 | 1/1999 |
| WO | WO 99/21615 | 5/1999 |
| WO | WO 00/06243 | 2/2000 |
| WO | WO 00/40275 | 7/2000 |
| WO | WO 00/71204 | 11/2000 |
| WO | WO 2004/096293 | 11/2004 |

OTHER PUBLICATIONS

Communication Pursuant to Article 94(3) EPC Dated Jul. 29, 2011 From the European Patent Office Re.: Application No. 09154192.0.
Official Action Dated Aug. 11, 2011 From the US Patent and Trademark Office Re. U.S. Appl. No. 10/554,743.
Official Action Dated Nov. 15, 2011 From the US Patent and Trademark Office Re. U.S. Appl. No. 12/547,516.
Milkey "Stability of Dilute Solutions of Uranium, Lead, and Thorium Ions", Analytical Biochemistry, 26: 1800-1803, 1954.
Stajnkrycer et al. "Chemical and Radiological Toxicity of Depleted Uranium", Military Medicine, 169(3): 212-216, Mar. 2004.
Tepe et al. "Prophylaxis of Restenosis With 186Re-Labeled Stents in a Rabbit Model", Circulation, 104: 480-485, 2001.
Official Action Dated Sep. 16, 2009 From the US Patent and Trademark Office Re.: U.S. Appl. No. 10/554,743.
Translation of Notice of Reason for Rejection Dated Oct. 30, 2009 From the Japanese Patent Office Re. 2006-507616.
Communication Pursuant to Article 94(3) EPC Dated Jan. 19, 2010 From the European Patent Office Re.: Application No. 09154192.0.
Office Action Dated Oct. 21, 2009 From the Israel Patent Office Re.: Application No. 171629 and Its Translation Into English.
Response Dated Dec. 16, 2009 to Official Action of Sep. 16, 2009 From the US Patent and Trademark Office Re.: U.S. Appl. No. 10/554,743.
Response Dated Feb. 21, 2010 to Notice of Reason for Rejection of Oct. 30, 2009 From the Japanese Patent Office Re. 2006-507616.
Response Dated Nov. 29, 2009 to Examiner's Report of Dec. 1, 2008 From the Australian Government, IP Australia Re.: Application No. 2004233763.

(Continued)

*Primary Examiner* — Michael G Hartley
*Assistant Examiner* — Melissa Perreira

(57) ABSTRACT

A radiotherapy method, comprising positioning a predetermined amount of a radionuclide selected from the group consisting of Radium-223, Radium-224, Radon-219 and Radon-220, in proximity to and/or within a tumor of a subject, for a predetermined time period. The predetermined amount and the predetermined time period are selected sufficient for the radionuclide to administering a predetermined therapeutic dose of decay chain nuclei and alpha particles into the tumor.

27 Claims, 7 Drawing Sheets

(56) References Cited

OTHER PUBLICATIONS

Office Action Dated Aug. 5, 2010 From the Israel Patent Office Re.: Application No. 171629 and Its Translation Into English.
Translation of Notice of Reason for Rejection Dated Sep. 10, 2010 From the Japanese Patent Office Re. 2006-507616.
Response Dated Mar. 1, 2011 to Notice of Reason for Rejection of Sep. 10, 2010 From the Japanese Patent Office Re. 2006-507616.
Examiner's Report Dated Apr. 27, 2011 From the Australian Government, IP Australia Re. Application No. 2010201870.
Official Action Dated Mar. 12, 2012 From the US Patent and Trademark Office Re.: U.S. Appl. No. 10/554,743.
Translation of Notice of Reason for Rejection Dated Jun. 10, 2011 From the Japanese Patent Office Re. 2006-507616.
Notice of the Reason for Rejection Dated Oct. 6, 2011 From the Korean Intellectual Property Office Re. Application No. 2011-7015686.
Response Dated Jul. 22, 2010 to Communication Pursuant to Article 94(3) EPC of Jan. 19, 2010 From the European Patent Office Re.: Application No. 09154192.0.
Requsition by the Examiner Dated Feb. 3, 2011 From the Canadian Intellectual Property Office Re. Application No. 2,523,646.
International Search Report and the Written Opinion Dated Nov. 16, 2004 From the International Searching Authority Re.: Application No. PCT/IL2004/000363.
Response Dated Feb. 15, 2005 to Communication Pursuant to Rule 43 bis 1 PCT of Nov. 16, 2004 From the European Patent Office (c/o International Preliminary Examination Authority) Re.: Application No. PCT/IL2004/000363.
Communication Pursuant to Article 96(2) EPC Dated Sep. 22, 2006 From the European Patent Office Re.: Application No. 04730355.7.
European Search Report and the European Search Opinion Dated Jul. 6, 2007 From the European Patent Office Re.: Application No. 07108380.2.
Examiner's Report Dated Dec. 1, 2008 From the Australian Government, IP Australia Re.: Application No. 2004233763.
Official Action Dated May 26, 2009 From the US Patent and Trademark Office Re.: U.S. Appl. No. 10/554,743.
Thomson et al. "Stereostatic Multiple Arc Radiotherapy", The British Journal of Radiology, 63(754): 745-751, 1990. Fig.5.
Response Dated May 20, 2010 to Office Action of Oct. 21, 2009 From the Israel Patent Office Re.: Application No. 171629.
Official Action Dated Jan. 28, 2011 From the US Patent and the Trademark Office Re. U.S. Appl. No. 10/554,743.
Response Dated Jan. 26, 2011 to Office Action of Aug. 5, 2010 From the Israel Patent Office Re.: Application No. 171629.
Translation of the Notice of the Reason for Rejection Dated Feb. 14, 2011 From the Korean Intellectual Property Office Re. Application No. 2005-7020659.
Examiner's Report Dated Apr. 11, 2011 From the Australian Government, IP Australia Re. Application No. 2010201870.
Office Action Dated Feb. 7, 2011 From the Israel Patent Office Re. Application No. 171629 and Its Translation Into English.
Office Action Dated Feb. 7, 2011 From the Israel Patent Office Re. Application No. 207737 and Its Translation Into English.
Office Action Dated Feb. 7, 2011 From the Israel Patent Office Re. Application No. 207738 and Its Translation Into English.
International Preliminary Report on Patentability Dated Jun. 22, 2005 From the International Examining Authority Re. Application No. PCT/IL2004/000363.
Official Action Dated Nov. 22, 2010 From the US Patent and the Trademark Office Re. U.S. Appl. No. 10/554,743.
Official Action Dated Sep. 29, 2010 From the US Patent and the Trademark Office Re. U.S. Appl. No. 10/554,743.
Response Dated Sep. 29, 2010 to Official Action of Apr. 1, 2010 From the US Patent and Trademark Office Re.: U.S. Appl. No. 10/554,743.
Official Action Dated Sep. 10, 2012 From the US Patent and Trademark Office Re. U.S. Appl. No. 12/547,516.
Translation of Notice of Reason for Rejection Dated Apr. 10, 2012 From the Japanese Patent Office Re. Application No. 2010-71442.
Kirby et al. "The Radiochemistry of Radium", National Academy of Sciences National Research Council, Nuclear Science Series, U.S. Atomic Energy Commission, p. 1-213, Dec. 1964.
Official Action Dated Dec. 10, 2012 From the US Patent and the Trademark Office Re. U.S. Appl. No. 10/554,743.
Free Dictionary "Embed", The Free Dictionary, 2012.
Official Action Dated Nov. 14, 2012 From the US Patent and Trademark Office Re. U.S. Appl. No. 12/547,515.
Wood "Displacement Current and Multiple Pulse Effects in Plasma Source Ion Implantation", Journal of Applied Physics, 73(10: 4770-4778, May 15, 1993.
Official Action Dated Oct. 25, 2013 From the US Patent and Trademark Office Re. U.S. Appl. No. 10/554,743.
Applicant-Initiated Interview Summary Dated Mar. 7, 2014 From the US Patent and Trademark Office Re. U.S. Appl. No. 10/554,743.

\* cited by examiner

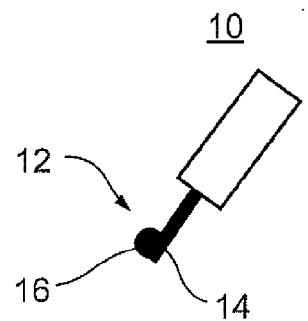
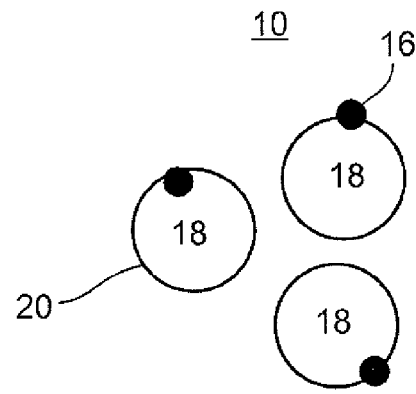
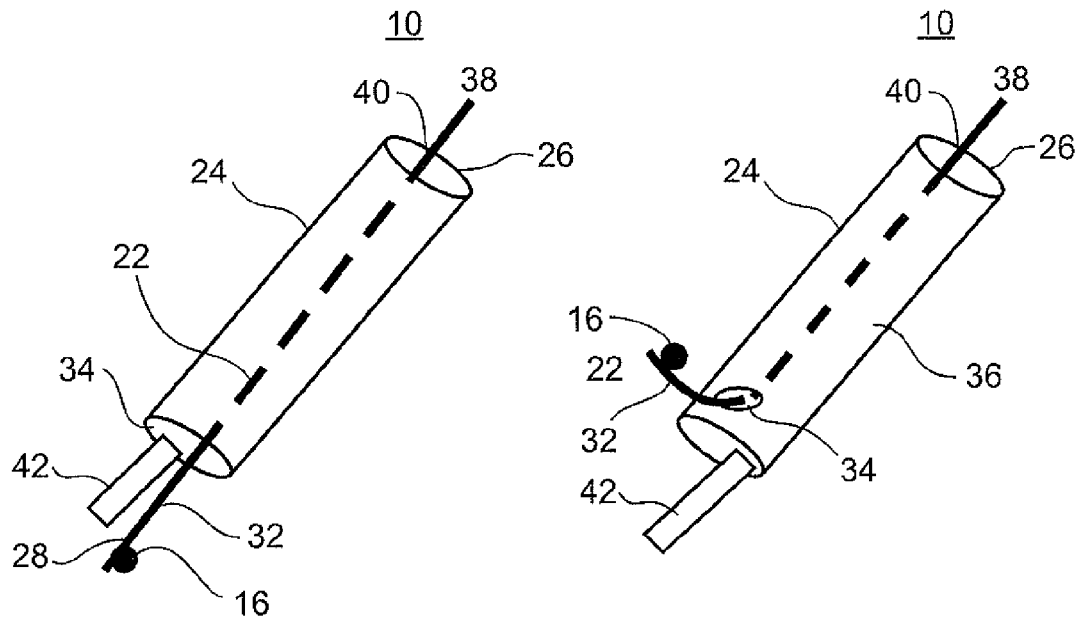
Fig. 1a  Fig. 1b  Fig. 1c  Fig. 1d

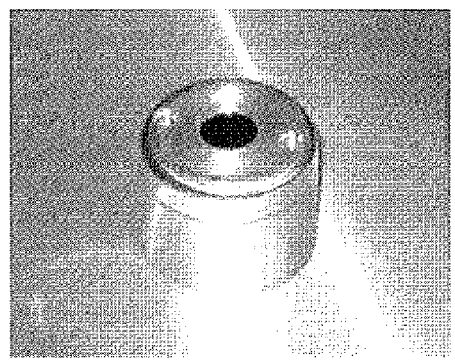
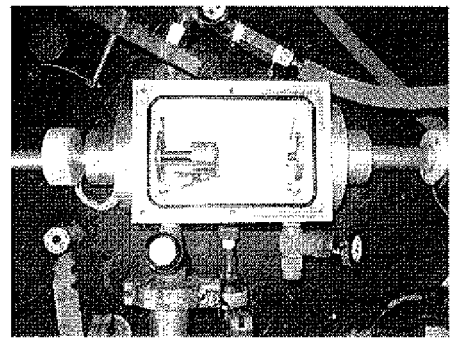
Fig. 2a                Fig. 2b
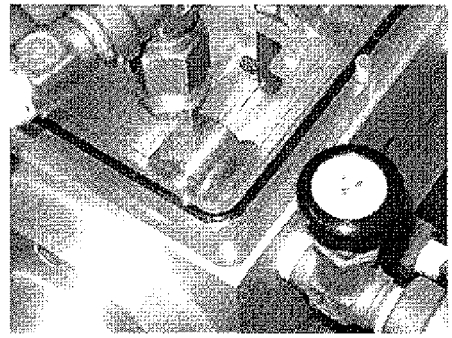
Fig. 2c
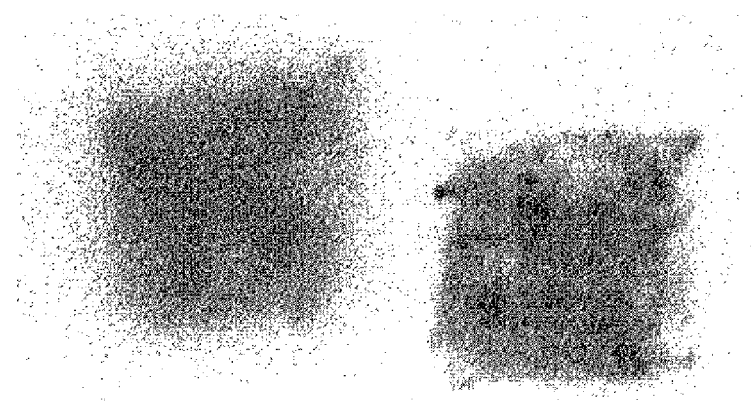
Fig. 3a                Fig. 3b ~3mm     ~2mm     ~3mm     ~0.7mm

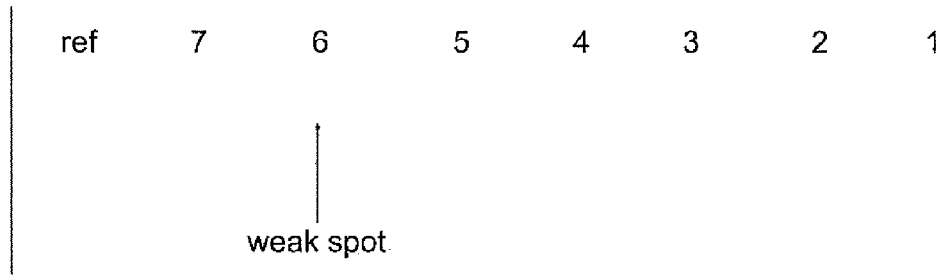
Fig. 9
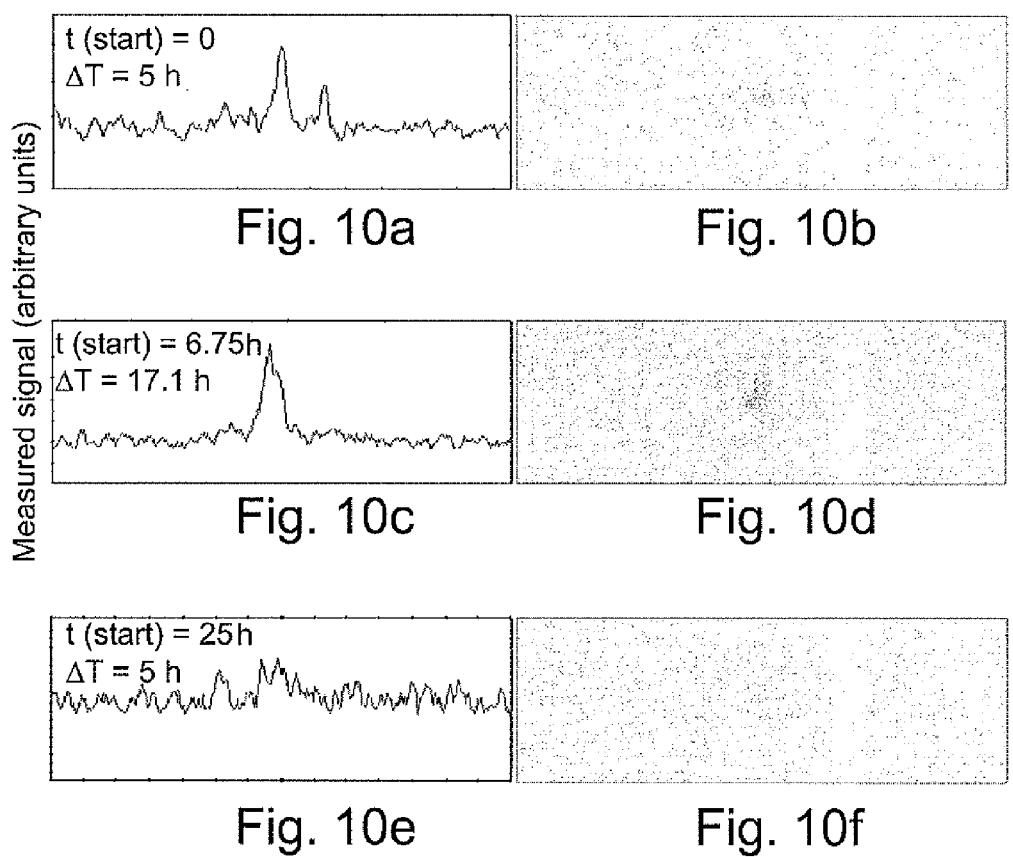
Fig. 10a  Fig. 10b
Fig. 10c  Fig. 10d
Fig. 10e  Fig. 10f

미국

US 8,834,837 B2

METHOD AND DEVICE FOR RADIOTHERAPY

RELATED APPLICATIONS

This application is a divisional filing of U.S. patent application Ser. No. 10/554,743, filed on Oct. 28, 2005, which is a US National Phase of PCT Patent Application No. PCT/IL2004/000363, filed on Apr. 29, 2004, which claims the benefit under 35 U.S.C. §119(e) of U.S. Provisional Patent Application No. 60/466,408, filed on Apr. 30, 2003. The contents of the above applications are all incorporated herein by reference.

FIELD AND BACKGROUND OF THE INVENTION

The present invention relates to radiotherapy and, more particularly, to a method and device for radiotherapy using decay chain nuclei of a radionuclide.

Cancer is a major cause of death in the modern world. Effective treatment of cancer is most readily accomplished following early detection of malignant tumors. Most techniques used to treat cancer (other than chemotherapy) are directed against a defined tumor site in an organ, such as brain, breast, ovary, colon and the like.

When a mass of abnormal cells is consolidated and is sufficiently large, surgical removal, destruction of the tumor mass using heating, cooling, irradiative or chemical ablation becomes possible because the target is readily identifiable and localizable. However, it is not uncommon for a cancer that has initially occurred at a primary site to metastasize and spread into adjacent organs as diffuse clusters of abnormal cells.

Known in the art are several procedures for treating tumors by irradiation. One such procedure employs laser light, which can destruct unwanted cells either through a direct interaction between the laser beam and the tissue, or through activation of some photochemical reactions using light-activated molecules which are injected into or otherwise administered to the tissue. For example, in a procedure, known as Photodynamic therapy (PDT), a photosensitive drug that binds to rapidly dividing cells is administered to the subject. Subsequently, the photosensitive drug is irradiated using a narrow-band laser so as to induce a chemical reaction resulting in a production of reactive products which then destroy the abnormal tissue.

The PDT technique suffers from a number of drawbacks and limitations. It is necessary to deliver a large amount of light radiation to the tumor at specific wavelengths to activate the photosensitive agent. Most photosensitive agents are activated at wavelengths that can only penetrate through three or less centimeters of tissue. Hence, non- or minimal-invasive PDT can be used for cancerous growths that are on or near the surface of the skin, or on the lining of internal organs.

Radiation therapy, also referred to as radiotherapy, or therapeutic radiology, is the use of radiation sources in the treatment or relief of diseases. Radiotherapy typically makes use of ionizing radiation, deep tissue-penetrating rays, which can physically and chemically react with diseased cells to destroy them. Each therapy program has a radiation dosage defined by the type and amount of radiation for each treatment session, frequency of treatment session and total of number of sessions.

Radiotherapy is particularly suitable for treating solid tumors, which have a well-defined spatial contour. Such tumors are encountered in breast, kidney and prostate cancer, as well as in secondary growths in the brain, lungs and liver.

Conventionally, the mainstream of the radiotherapy is toward the so-called treatment through external irradiation, that is, treating an internal tumor grown in a human subject with a radiation of an external source (e.g., of gamma rays). Alternatively, a radioactive source (typically an electron emitting source) is inserted into the body.

To avoid adversely affecting any healthy region of the subject, one attempts to maximize the dose administered to the target zone (to ensure killing the cancerous cells) while minimizing the dose to other regions (to avoid undesirable damage). Most commonly, radiotherapy is used as an adjunct way of use, such as treating those remnant, not entirely removed, tumor cells by being exposed to a radiation dose of an external source after the surgical opening of the human body, removal of malignant tumors and the suture of the body parts or radiating the radiation dose directly to the remnant tumor cells before the suture of the body parts involved.

It is well known that different types of radiation differ widely in their cell killing efficiency. Gamma and beta rays have a relatively low efficiency. By contrast, alpha particles as well as other heavy charged particles are capable of transferring larger amount of energies, hence being extremely efficient. In certain conditions, the energy transferred by a single heavy particle is sufficient to destroy a cell. Moreover, the non-specific irradiation of normal tissue around the target cell is greatly reduced or absent because heavy particles can deliver the radiation over the distance of a few cells diameters.

On the other hand, the fact that their range in human tissue is less than 0.1 millimeter, limits the number of procedures in which heavy particles can be used. More specifically, conventional radiotherapy by alpha particles is typically performed externally when the tumor is on the surface of the skin.

There is thus a widely recognized need for, and it would be highly advantageous to have a method and device for radiotherapy using alpha particles and decay chain nuclei of a radionuclide, devoid of the above limitations.

SUMMARY OF THE INVENTION

According to one aspect of the present invention there is provided a radiotherapy method, comprising positioning a predetermined amount of a radionuclide selected from the group consisting of Radium-223, Radium-224, Radon-219 and Radon-220, in proximity to and/or within a tumor of a subject, for a predetermined time period, the predetermined amount and the predetermined time period selected sufficient for the radionuclide to administer a predetermined therapeutic dose of decay chain nuclei and alpha particles into the tumor.

According to further features in preferred embodiments of the invention described below, the method further comprises removing the radionuclide of the tumor once the predetermined therapeutic dose of decay chain nuclei and alpha particles is administered.

According to another aspect of the present invention there is provided a method of removing a tumor and remnants thereof present in a body of a subject, the method comprising: (a) debulking at least a portion of the tumor and exposing tissue surrounding the tumor; and (b) positioning a predetermined amount of a radionuclide selected from the group consisting of Radium-223, Radium-224, Radon-219 and Radon-220, in proximity to and/or within the surrounding tissue, for a predetermined time period, the predetermined amount and the predetermined time period selected sufficient for the radionuclide to administer a predetermined therapeutic dose of decay chain nuclei and alpha particles into the surrounding tissue.

According to further features in preferred embodiments of the invention described below, the debulking is performed laparoscopically.

According to still further features in the described preferred embodiments the debulking is performed endoscopically.

According to still further features in the described preferred embodiments the debulking is performed surgically.

According to still further features in the described preferred embodiments the debulking is performed ablatively.

According to still further features in the described preferred embodiments the debulking is by a laser beam.

According to still further features in the described preferred embodiments the debulking comprises applying heat to the tumor.

According to still further features in the described preferred embodiments the debulking is by a microwave antenna.

According to still further features in the described preferred embodiments the debulking is by a radiofrequency electrode.

According to still further features in the described preferred embodiments the debulking is by an ultrasound device.

According to still further features in the described preferred embodiments the positioning of the radionuclide is by at least one radiotherapy device having a surface whereby the radionuclide is on or beneath the surface.

According to still further features in the described preferred embodiments the radiotherapy device comprises a needle.

According to still further features in the described preferred embodiments the radiotherapy device comprises at least one bead.

According to still further features in the described preferred embodiments the radionuclide is soluble in a solute and further wherein the positioning the radionuclide comprises administering to the subject in proximity to and/or within the tumor a solution of the radionuclide in the solute.

According to still further features in the described preferred embodiments the method further comprising recording a dose of the alpha particles.

According to still further features in the described preferred embodiments the recording is by a sheet of photoluminescent material.

According to still further features in the described preferred embodiments the recording is by a sheet of photostimulable phosphor.

According to still further features in the described preferred embodiments the predetermined time is from about 10 seconds to about 10 hours.

According to still further features in the described preferred embodiments the predetermined time is a few days.

According to an additional aspect of the present invention there is provided a radiotherapy device, comprising a probe adapted for being at least partially introduced into a body of a subject, and a radionuclide selected from the group consisting of Radium-223 and Radium-224, the radionuclide being on or beneath a surface of the probe, in a manner such that decay chain nuclei and alpha particles of the radionuclide are emitted outside the surface.

According to further features in preferred embodiments of the invention described below, the probe is coated by a protective coat.

According to still further features in the described preferred embodiments at least one of a thickness and a material of the protective coat is selected so as not to prevent the emission of the decay chain nuclei and the alpha particles.

According to still further features in the described preferred embodiments the probe comprises an inner elongated member and an outer tubular member having a mouth section configured for receiving the inner elongated member, the inner elongated member being movable within the outer tubular member and having a distal end and a proximal end, whereby the radionuclide is on or beneath a surface of the distal end.

According to still further features in the described preferred embodiments the device further comprising an operating wire, connected to the proximal end of the inner elongated member.

According to still further features in the described preferred embodiments the device further comprising a detector, capable of detecting the radionuclide, the decay chain nuclei and the alpha particles.

According to still further features in the described preferred embodiments the detector is operatively associated with the probe.

According to still further features in the described preferred embodiments the detector is adapted for being inserted through the mouth section.

According to still further features in the described preferred embodiments the detector comprises a photoluminescent material.

According to still further features in the described preferred embodiments the detector comprises a photostimulable phosphor.

According to still further features in the described preferred embodiments the probe is capable of releasing at least a portion of the radionuclide therefrom, thereby allowing distribution of the radionuclide prior to the emission of the decay chain nuclei and alpha particles.

According to still further features in the described preferred embodiments the release of the at least a portion of the radionuclide is by body fluids.

According to yet another aspect of the present invention there is provided a method of manufacturing a radiotherapy device, the method comprising: (a) providing a probe having a surface; (b) positioning the surface in a flux of a radionuclide; and (c) collecting nuclei of the radionuclide on or beneath the surface; thereby manufacturing the radiotherapy device.

According to further features in preferred embodiments of the invention described below, the collecting is by direct implantation in a vacuum.

According to still further features in the described preferred embodiments the collecting is by connecting the surface to a voltage source of negative polarity.

According to still further features in the described preferred embodiments the positioning of the surface in the flux of the radionuclide is in a gaseous environment.

According to still further features in the described preferred embodiments a pressure of the gaseous environment and a voltage of the voltage source are selected such that a velocity of nuclei is reduced to a thermal velocity.

According to still further features in the described preferred embodiments the steps (b) and (c) are done in a manner such that decay chain nuclei and alpha particles of the radionuclide are emitted outside the surface.

According to still further features in the described preferred embodiments the probe comprises at least one needle.

According to still further features in the described preferred embodiments the probe comprises at least one bead.

According to still further features in the described preferred embodiments the probe is a tip of an endoscope.

According to still further features in the described preferred embodiments the probe is a tip of a laparoscope.

According to still further features in the described preferred embodiments the probe is a tip of an imaging device.

According to still further features in the described preferred embodiments the probe comprises an inner elongated member and an outer tubular member having a mouth section configured for receiving the inner elongated member, the inner elongated member being movable within the outer tubular member and having a distal end and a proximal end, whereby the radionuclide is collected on or beneath a surface of the distal end.

According to still further features in the described preferred embodiments the outer tubular member comprises at least one window, for allowing protrusion of the distal end of the inner elongated member therethrough.

According to still further features in the described preferred embodiments at least one window is on a side wall of the outer tubular member.

According to still further features in the described preferred embodiments the outer tubular member is made of a material capable of absorbing the decay chain nuclei and the alpha particles.

According to still further features in the described preferred embodiments the inner elongated member and the outer tubular member are each independently flexible.

According to still further features in the described preferred embodiments the method further comprising coating the surface by a protective coat.

According to still further features in the described preferred embodiments at least one of a thickness and a material of the protective coat is selected so as not to prevent emission of decay chain nuclei and alpha particles from the surface of the probe.

According to still further features in the described preferred embodiments an outgoing flux of the decay chain nuclei is from about $10^2$ to about $10^5$ atoms/sec.

According to still further features in the described preferred embodiments a surface density of the radionuclide is from about $10^{10}$ to about $10^{13}$ atoms/cm$^2$.

According to still further features in the described preferred embodiments the probe is capable of administering from about 100 rem to about 100000 rem of radiation.

According to still further features in the described preferred embodiments the probe is capable of administering from about 1000 to about 10000 rem of radiation.

According to still further features in the described preferred embodiments an activity of the radionuclide is from about 10 nanoCurie to about 10 microCurie.

According to still further features in the described preferred embodiments an activity of the radionuclide is from about 10 nanoCurie to about 1 microCurie.

According to still another aspect of the present invention there is provided a method of preparing a radioactive surface source, the method comprising: (a) providing a solution containing a predetermined amount of a radioactive isotope; and (b) spreading the solution on a metal surface so as to provide an admixture of the metal and the solution; thereby providing the radioactive surface source.

According to further features in preferred embodiments of the invention described below, the solution is acidic solution.

According to still further features in the described preferred embodiments the radioactive isotope comprises Uranium-232.

According to still further features in the described preferred embodiments the radioactive isotope comprises uranyl chloride.

According to still further features in the described preferred embodiments the acidic solution comprises hydrochloric acid.

According to still further features in the described preferred embodiments the metal surface is prepared by evaporating at least one metal on a substrate.

According to still further features in the described preferred embodiments the metal surface comprises at least one metal selected from the group consisting of nickel, molybdenum and palladium.

According to still further features in the described preferred embodiments the substrate is made of silicon.

According to still further features in the described preferred embodiments the method further comprising cooling the metal prior to the spreading the layer of the acidic solution thereon.

According to still further features in the described preferred embodiments the method further comprising applying a flow of gas on the metal, substantially contemporaneously with the spreading the layer of the acidic solution.

According to still further features in the described preferred embodiments the gas is air.

The present invention successfully addresses the shortcomings of the presently known configurations by providing a method, and device capable of performing radiotherapy using alpha radiation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a schematic illustration of a radiotherapy device, according to a preferred embodiment of the present invention;

FIG. 1b is a schematic illustration of the radiotherapy device, in a preferred embodiment in which beads are employed;

FIG. 1c is a schematic illustration of the radiotherapy device, in a preferred embodiment in which, the device comprises an inner elongated member and an outer tubular member;

FIG. 1d is a schematic illustration of the radiotherapy device of FIG. 1c, in a preferred embodiment in which the inner elongated member protrudes through a window formed in a wall of the outer tubular member;

FIGS. 2a-c show experimental setup of an experiment in which a radionuclide was embedded on a needle, using electrostatic forces, according to a preferred embodiment of the present invention;

FIGS. 3a-b show activity distribution of a collector (FIG. 3a) and a source (FIG. 3b) in an experiment in which a surface source of U-232 was prepared, according to a preferred embodiment of the present invention;

FIG. 6a is an image recorded by the detecting probe of FIG. 4a;

FIG. 6b is a radiation graph corresponding to the image of FIG. 6a;

FIG. 7a is an image recorded by the detecting probe of FIG. 4b;

FIG. 7b is a radiation graph corresponding to the image of FIG. 7a;

FIG. 8b is a radiation graph corresponding to the image of FIG. 8a;

FIG. 9 is an image of radiation patterns of the slices of FIG. 5; and

FIGS. 10a-f are images (FIGS. 10a, 10c and 10e) and corresponding radiation graphs (FIGS. 10b, 10d and 10f, respectively) of three consecutive radiation measurements in an experiment on mice having a B-16 Melanoma.

DESCRIPTION OF THE PREFERRED EMBODIMENTS

Figures 4A, 4B, 4C, 4D:
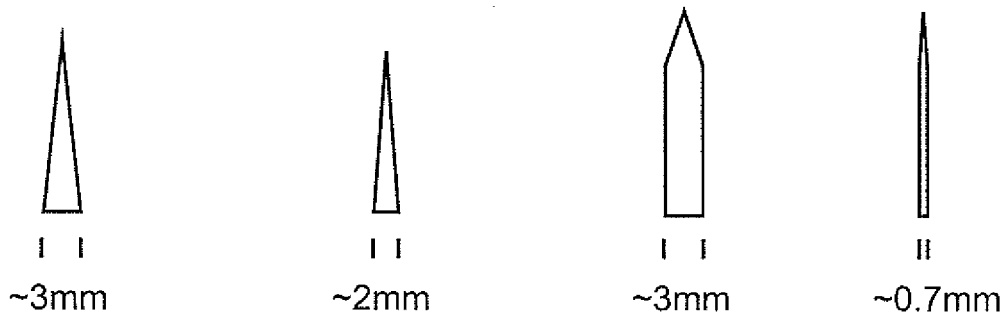
FIGS. 4a-d are schematic illustrations of detecting probes used in an in vivo experiment on mice having a LAPC4 prostate tumor, according to a preferred embodiment of the present invention.

The present invention is of a method and device which can be used in radiotherapy. Specifically, the present invention can be used to locally destroy tumors in either invasive or non-invasive procedures utilizing decay chain nuclei of a radionuclide, such as, but not limited to, Radium-223, Radium-224, Radon-219 and Radon-220.

The principles and operation of a method and device for radiotherapy according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Radiation is a flow of subatomic or atomic particles or waves, which can be emitted by nuclei of a radioactive substance when the nuclei undergo decay processes. One typically encounters four types of radiation: (i) alpha radiation, in a form of helium nuclei, also referred to as alpha particles; (ii) beta radiation, in a form of electrons or positrons, (iii) gamma radiation, in a form of electromagnetic waves or photons; and (iv) neutron radiation, in a form of neutral nucleons.

The rate at which nuclei of a radioactive substance undergo decay and emit radiation is directly proportional to the number of radioactive nuclei in the substance that can decay. Hence, as time goes on, the number of radioactive nuclei in the substance is reduced, and the decay rate decreases. The period of time over which the number of radioactive nuclei of a radioactive substance decreases by a factor of one-half, is referred to as the half-life of the substance. In general, radioactive decay is a quantum mechanical process governed by wavefunctions the square of which is interpreted as probability. In a short period of time, each radioactive nucleus has a certain probability of decaying, but whether it actually does is determined by random chance. When a radioactive nucleus has more than one decay channels, the probability of decaying in a certain channel is referred to as the branching ratio of the channel.

Nuclei which emit alpha particles, also known as alpha emitters, are typically heavy nuclei in which the ratio of neutrons to protons is too low. Following emission of an alpha particle (two protons and two neutrons) from such a nucleus, the ratio is increased and the nucleus becomes more stable. Since the number of protons in the nucleus of an atom determines the element, the loss of an alpha particle actually changes the atom to a different element. For example, Polonium-210 (Po) has 126 neutrons and 84 protons, corresponding to a ratio of 3:2. When an atom of Po-210 emits an alpha particle, the ratio is increased by about 1%, resulting in a stable Lead-206 (Pb) atom, having 124 neutrons and 82 protons.

Of the aforementioned four types of radiations, alpha particles are the heaviest, about 7000 times the electron's mass, and have the shortest range in human tissue, less than 0.1 millimeter. Conventional radiotherapy procedures by alpha particles are therefore effective only for tumors on or close beneath the surface of the skin.

While conceiving the present invention it has been hypothesized and while reducing the present invention to practice it has been realized that radiotherapy by alpha radiation can be employed also for tumors deep inside the body.

Hence, according to one aspect of the present invention there is provided a radiotherapy method, in which a predetermined amount of a radionuclide is positioned in proximity to and/or within a tumor of a subject, for a predetermined time period.

As used herein "in proximity to a tumor" refers to a sufficient distance for allowing alpha particles or decay chain nuclei of the radionuclide to arrive at the tumor. Preferably, the distance between the radionuclide and the tumor is below 0.1 mm, more preferably below 0.05 mm, most preferably below 0.001 mm.

According to a preferred embodiment of the present invention, the predetermined amount of radionuclide and the predetermined time period are preferably selected sufficient for the radionuclide to administer a predetermined therapeutic dose of decay chain nuclei and alpha particles into the tumor.

The radionuclide is preferably a relatively short lived radio-isotope, such as, but not limited to, Radium-223, Radium-224, Radon-219, Radon-220 and the like. When Radium 223 is employed, the following decay chain is emitted therefrom:

Ra-223 decays, with a half-life period of 11.4 d, to Rn-219 by alpha emission;

Rn-219 decays, with a half-life period of 4 s, to Po-215 by alpha emission;

Po-215 decays, with a half-life period of 1.8 ms, to Pb-211 by alpha emission;

Pb-211 decays, with a half-life period of 36 m, to Bi-211 by beta emission;

Bi-211 decays, with a half-life period of 2.1 m, to Tl-207 by alpha emission; and Tl-207 decays, with a half-life period of 4.8 m, to stable Pb-207 by beta emission.

As can be understood from the above decay chain, when Rn-219 is employed as the radionuclide, the decay chain begins with the decay of Rn-219 to Po-215, and continues to Pb-211, Bi-211, Tl-207 and Pb-207.

When Radium 224 is employed, the following decay chain is emitted therefrom:

Ra-224 decays, with a half-life period of 3.7 d, to Rn-220 by alpha emission;

Rn-220 decays, with a half-life period of 56 S, to Po-216 by alpha emission;

Po-216 decays, with a half-life period of 0.15 s, to Pb-212 by alpha emission;

Pb-212 decays, with a half-life period of 10.6 h, to Bi-212 by beta emission;

Bi-212 decays, with a half-life of 1 h, to Tl-208 by alpha emission (36% branching ratio), or to Po-212 by beta emission (64% branching ratio);

Tl-208 decays, with a half-life of 3 m, to stable Pb-208 by beta emission; and

Po-212 decays, with a half-life of 0.3 μs, to stable Pb-208 by alpha emission.

As can be understood from the above decay chain, when Rn-220 is employed as the radionuclide, the decay chain begins with the decay of Rn-220 to Po-216, and continues to Pb-212, Bi-212, Tl-208 (or Po-212) and Pb-208.

In any event when the radionuclide is positioned in proximity to and/or within a tumor, a plurality of short-lived atoms are released into the surrounding environment and dispersed therein by thermal diffusion and/or by convection via body fluids. The short-lived atoms and their massive decay products (i.e., alpha particles and daughters nuclei), either interact with the cells of the tumor or continue the decay chain by producing smaller mass particles. As will be appreciated by one ordinarily skilled in the art, the close proximity between the radionuclide and the tumor, and the large number of particles which are produced in each chain, significantly increase the probability of damaging the cells of interest, hence allowing for an efficient treatment of the tumor.

The method of the present invention can be employed either as a stand alone procedure or as a supplementary method to conventional debulking procedures for surgically removing or ablating a tumor. In typical conventional debulking procedures, once the tumor is removed, remnants of the tumor may be still present in tissue surrounding the region which was surgically removed or ablated. Hence, according to a preferred embodiment of the present invention the radionuclide can be positioned in proximity or within the surrounding tissue, again, for a predetermined time period, so as to administer the decay chain nuclei and alpha particles into the surrounding tissue.

This embodiment can be employed subsequently or contemporaneously to any debulking procedure known in the art, including, without limitation a full invasive procedure, a laparoscopic procedure and an endoscopic procedure. Many methods of debulking tumors are contemplated. For example, in one embodiment the debulking procedure is performed surgically, e.g., by dissecting the tumor or the surrounding tissue using a conventional scalpel or any other mechanical device; in another embodiment the debulking procedure is performed ablatively, e.g., by heating or irradiating the tumor, for example, by laser or ultrasonic radiation. The above and other procedures may include the use of a laser device, microwave antenna, a radiofrequency electrode, an ultrasound device and the like.

According to a preferred embodiment of the present invention, the radionuclide can be inserted into the body of the subject and positioned in proximity to and/or within the tumor by more than one way.

Hence, in one embodiment, the radionuclide is soluble in a solute and the positioning of the radionuclide is by administering a solution of the radionuclide in the solute to the subject in proximity to and/or within the tumor. In another embodiment, the positioning of the radionuclide is by at least one radiotherapy device, whereby the radionuclide is on or beneath a surface of the device. A method of preparing a surface having the radionuclide is provided hereinafter and amplified in the Examples section that follows.

Referring now to the drawings, FIGS. 1a-d illustrate a radiotherapy device 10, in accordance with preferred embodiments of the invention. In the embodiment shown in FIG. 1a, device 10 is preferably a probe 12 whereby radionuclide 16 is on or beneath a surface 14 of probe 12. Probe 12 can be, for example, a needle, or any other device adapted for being at least partially introduced into a body of a subject. Representative examples include, without limitation, a tip of an endoscope, a tip of a laparoscope and a tip of an imaging device.

Referring to FIG. 1b, in another embodiment, device 10 comprises one or more beads 18 whereby radionuclide 16 is on or beneath a surface 20 of beads 18. Beads 18 can be distributed near or in the tumor, for example by injection or during an invasive procedure.

Referring to FIGS. 1c-d, in an additional embodiment, device 10 comprises an inner elongated member 22 and an outer tubular member 24, each independently can be rigid or flexible. Tubular member 24 is preferably manufactured with a mouth section 26 configured for receiving inner member 22. Inner member 22 is preferably capable of moving, either longitudinally or rotationally within tubular member 24. Radionuclide 16 is on or beneath a surface 28 of a distal end 32 of inner member 22. When inner member 22 protrudes out of a window 34 of tubular member 24, many locations within the body of the subjects can be reached so as to bring radionuclide 16 into close proximity to the tumor. As shown in FIG. 1d, window 34 can be formed in a side wall 36 of tubular member 24, so as to facilitate rotational motion of device 10 and to allow inner member 22 to reach different portions of the body.

According to a preferred embodiment of the present invention device 10 can also comprise an operating wire 38, connected to a proximal end 40 of inner member 22. Wire 38 serves for operating device 10 through the body of the subject. More specifically, wire 38 can be used by the operator for providing inner member 22 with its longitudinal and/or rotational motion.

Tubular 24 can be made of a material which absorbs the decay chain nuclei and alpha particles of radionuclide 16, so that when distal end 32 of inner member 22 does not protrude through window 34 radiation is at least partially blocked. This embodiment is particularly useful when it is desired to temporarily cease the emission of radiation from device 10 to the body of the subject, for example when during the delivery of device 10 to the tumor, or to prevent interference with a certain measurement which may be performed simultaneously with the radiotherapy procedure.

The advantage of using device 10 for positioning radionuclide 16 is that when radionuclide 16 is confined to device 10, convection of radioactive material away from the tumor is substantially prevented. One of ordinary skill in the art will appreciate that although a small portion of the decay chain nuclei, emitted by radionuclide 16 can, in principle, be transported to healthy regions by body fluids, the effect of this portion on the healthy tissue is minimized. Being spread in large volume, the transported portion is extremely ineffective due to very small energy/mass ratio. Thus, with reference to the above decay chains, when device 10 comprises, for example, Ra-224, the Ra-224 atoms preferably remain in device 10 while the other decay chain nuclei and alpha particles are emitted therefrom. As the main radiation source is the Ra-224, the confinement of Ra-224 to device 10 allows irradiating a predetermined volume of tissue surrounding device 10, while substantially preventing damage to regions beyond the predetermined volume.

It is to be understood, that it is not intended to limit the scope of the present invention solely to radionuclide which is confined to device 10. In some embodiments of the present invention, once radionuclide 16 is delivered to a predetermined position it can be released from device 10, for example, by allowing body fluids to wash radionuclide 16 off device 10.

According to a preferred embodiment of the present invention device 10 can comprise a detector 42, for detecting alpha particles, radionuclide 16 or its decay chain nuclei. This embodiment is particularly useful when it is desired to monitor or record the amount of radiation which was delivered to the respective portion of the body of the subject. Detector 42 can be connected to tubular member 24 or inner member 22, in which case detector 42 is preferably adapted for being inserted through mouth section 26. Alternatively, detector 42 can be detached from tubular member 24 or inner member 22, so as to allow separate insertion of detector 42 into the body. Detector 42 can be for example, a sheet of a photoluminescent material, such as, but not limited to, a storage phosphor.

Storage phosphors, also known as photostimulable phosphors are commonly used in radiography. Generally, storage phosphors retain a latent image when exposed to a two dimensional pattern of radiation, analogous to film. The image is stored by exposing the molecules of the photostimulable phosphors to the radiation thereby exciting them to a long-lived isomeric state. After the exposure to the radiation, the latent image can be read out by aiming a stimulating beam of light at detector 42. The stimulating beam further excites the molecules to a higher state from which they decay back by emitting a photon. The emitted photons in turn can be converted into an electronic form by a suitable device, e.g., a photo multiplier tube (not shown) for further processing. As further demonstrated in the example section that follows, detector 42 is capable of detecting individual alpha particles.

As stated, the amount of radionuclide 16 which is inserted into the body of the subject and the time period during which radionuclide 16 emits radiation, are preferably selected sufficient so as to administer a predetermined therapeutic dose of decay chain nuclei and alpha particles into the tumor. The radiation dose reflects the accumulated amount of energy deposited by the radiation in a unit mass. Typically, radiation dose is measured in units of rads, where one rad is equivalent to 100 ergs/gr. In radiotherapy it is common to measure radiation doses in units of rems, which reflect the damage incurred in the tissue due to the radiation. For alpha particles, the one rad is equivalent to about 20 rems.

The amount of radiation provided radionuclide 16 is preferably from about 100 rem to about 100000 rem, more preferably, from about 1000 to about 10000 rem. In terms of particles flux, the outgoing flux of decay chain nuclei of radionuclide 16 is from about $10^2$ to about $10^5$ atoms/sec, more preferably from about $10^3$ to about $10^4$ atoms/sec.

As used herein the term "about" refers to ±10%.

According to a preferred embodiment of the present invention the delivery of the aforementioned doses and fluxes can be done on more than one time scale. Hence, in one embodiment, radionuclide 16 is inserted into the body of the subject and allowed to completely decay in situ.

As used herein "a complete decay" of a radionuclide refers to an activity is reduction thereof by at least 98%.

The embodiment in which radionuclide 16 completely decays can be executed, for example, when device 10 comprises beads 18, or when radionuclide 16 is soluble in a solution, as further detailed hereinabove. Alternatively, this embodiment can be executed by temporarily implanting a tip of a needle (see, e.g., FIG. 1a) with radionuclide 16 in proximity or near the tumor, and allowing radionuclide 16 to completely decay. Subsequently, the implantation can be removed.

The advantage of allowing radionuclide 16 to completely decay, it that in this embodiment the therapeutic dose of decay chain nuclei and alpha particles is delivered over a relatively long period, during which the time dependence of the radiation has a typical shape of a decaying exponent, characterized by a half-life of radionuclide 16. For example, if radionuclide 16 is Ra-224 the time dependence is characterized by a half-life of 3.7 days, and if radionuclide 16 is Ra-223, the time dependence is characterized by a half-life of 11.4 days.

According to a preferred embodiment of the present invention, when radionuclide 16 is allowed to completely decay in situ, the total time of treatment is from about 4 hours to about 70 days, for example, 4 hours, 3 days, 20 days and the like.

In another embodiment, radionuclide 16 is positioned in proximity to and/or within a tumor of a subject, allowed to emit its decay chain nuclei and alpha particles, and, after a predetermined time period, removed from the body of the subject, preferably before a complete decay of radionuclide 16. This embodiment can be executed, for example, using device 10 or any other medical instrument which can be inserted and extracted as desired. Suitable shapes of device 10 for this embodiment include, without limitations, a sufficiently long needle or any of the configurations shown in FIGS. 1a, 1c and 1d. Additionally, device 10 can comprise an endoscope tip, a laparoscope tip, an imaging device tip and the like, as further detailed hereinabove.

The advantage of this embodiment is that during the time period in which radionuclide 16 is in the body, the device 10 can be repositioned, thereby making the treatment more selective in terms of the cells being destroyed. When device 10 is in place near or inside the tumor, the radiation rate is dominated by the decay rate of radionuclide 16, and is therefore substantially constant. Once extracted the decay chain nuclei which were emitted from device 10 remain in the body and continue to decay. The time dependence of the radiation one device 10 is extracted, has a typical shape of a decaying exponent, characterized by a half-life of the longest lived decay chain nucleus. For example, if radionuclide 16 is Ra-224 the time dependence is characterized by the half-life of Pb-212 (10.6 hours), and if radionuclide 16 is Ra-223, the time dependence is characterized by the half-life of Pb-211 (36 minutes).

According to a preferred embodiment of the present invention, when radionuclide 16 is temporarily inserted into the body, the total time of treatment is from 10 seconds to a few hours, for example, 1 minute, 10 minutes, 20 minutes and the like.

Whether radionuclide 16 is removed prior to its complete decay or allowed to completely decay in situ, its activity is selected so as to allow the administration of the aforementioned therapeutic dose into the tumor. The relation between the activity of radionuclide 16 and the administered dose may depend on many factors such as, but not limited to, the type and size of the tumor, the number of locations to which radionuclide 16 is inserted (for example, when more than one radiotherapy device is used), the distance between radionuclide 16 and the tumor and the like. A typical activity of radionuclide 16 is, without limitation, from about 10 nanoCurie to about 10 microCurie, more preferably from about 10 nanoCurie to about 1 microCurie.

The method and device of the present invention can be used to destroy many tumors. Typical tumors include, but are not limited to, breast tumor, brain tumor, neuroblastoma, thyroid gland tumor, gestational trophoblastic tumor, uterine sarcoma, carcinoid tumor, colon carcinoma, esophageal carcinoma, hepatocellular carcinoma, liver carcinoma, lymphoma, plasma cell neoplasm, mesothelioma, thymoma, alveolar soft-part sarcoma, angiosarcoma, epitheloid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, synovial sarcoma, melanoma, neuroepithelioma, osteosarcoma, leiomyosarcoma, Ewing sarcoma, osteosarcoma, rhabdomyo-sarcoma, hemangiocytoma, myxosarcoma, mesothelioma (e.g., lung mesothelioma), granulosa cell tumor, thecoma cell tumor and Sertoli-Leydig tumor.

Hence, the method and device of the present invention can be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

According to an additional aspect of the present invention there is provided a method of manufacturing a radiotherapy device, e.g., device 10. The method comprises the following method steps in which in a first step, a probe having a surface is provided, in a second step, the surface is positioned in a flux of a radionuclide, e.g., radionuclide 16, and in a third step, nuclei of the radionuclide are collected on or beneath the surface.

According to a preferred embodiment of the present invention the collection of the radionuclide on the probe is done in a manner such that the natural recoil energy of the daughter nucleus of the radionuclide (typically of the order of 100 keV), is sufficiently large so as to allow the daughter nucleus to escape the surface of the probe. This can be done by embedding the radionuclide on or beneath the surface of the probe, typically at a depth of the order of about 10 nanometers. Optionally and preferably, the outer layer of the probe can be made of a porous material so as to increase the probability of the escape.

As stated, radionuclide 16 is preferably a relatively short lived radio-isotope (e.g., Ra-224 or Ra-223), with a half-life of a few days. Thus, according to a preferred embodiment of the present invention, the collection of the radionuclide on the probe is done with a minimal delay prior to its application. This can be achieved, for example, through the utilization of a flux generating surface source. For example, when the radionuclide is Ra-224, a flux thereof can be generated by a surface source of Th-228. A surface source of Th-228 can be prepared, for example, by collecting Th-228 atoms emitted from a parent surface source of U-232. Such parent surface source can be prepared, for example, by spreading a thin layer of acid containing U-232 on a metal. A representative example of preparing a surface source of Th-228 from U-232 is provided hereinafter in the Examples section that follows.

Alternatively, a surface source of Th-228 can be obtained by collecting a beam of Fr-228 having a half-life of 39 seconds, which in turn decays to Ra-228. The Ra-228 decays, with a half-life of 5.75 years, to Ac-228 which in turn decays, with a half-life of 6 hours, by beta decay, to Th-228. The entire decay chain, Fr-228, Ra-228, Ac-228 and Th-228 is by beta emission. The population of Th-228 is slowly built over a period of the order of a few years, approaching radioactive equilibrium with Ra-228. Thus, the obtained Th-228 surface source is characterized by the 5.75 years half-life of Ra-228 rather than by its own 1.9 years half-life.

When the radionuclide is Ra-223, a flux thereof can be generated by a surface source of Ac-227, which is in radioactive equilibrium with Th-227. An Ac-227 surface source can be obtained by separating a beam of Fr-227 ions having an energy of a few tens of keV, and implanting the Fr-227 ions in a foil at a depth of a few nanometers. Through a sequence of two short half-life beta decays, the Fr-227 ions decay to Ac-227, thereby providing the desired Ac-227 surface source.

Available isotope separators for separating the Fr-227 or Fr-228 include, without limitation, ISOLDE, located at CERN, Geneva or ISAC, located at TRIUMF, Vancouver.

The collection of the radionuclide on or beneath the surface of the probe can be done in more than one way. For example, in one embodiment, the collection is by direct implantation in a vacuum. In this embodiment, the surface source which generates the radionuclide flux is placed in vacuum in close proximity to the probe. Nuclei recoiling from the surface source traverse the vacuum gap and being implanted in the surface of the probe.

In an alternative embodiment, the collection is done by electrostatic forces. As the desorbing atoms from the surface source are positively charged (both due to the decay itself and as a result of passage through layers of the surface source material), an application of a suitable negative voltage between the surface source and the probe, the desorbing nuclei of the radionuclide can be collected onto the outer surface of the probe. According to a preferred embodiment of the present invention, the collection is done under suitable gas pressure, so as to slow the velocity of the nuclei to a thermal velocity, hence facilitating their collection of the probe. According to a preferred embodiment of the present invention, the area of the probe is substantially smaller than the area of the surface source. Due to the electrostatic forces between the probe and the desorbing atoms, substantially all the atoms desorbed from the surface source are captured on the surface of the probe. One ordinarily skilled in the art would appreciate that as the area of the probe is smaller than the area of the surface source, a high concentration of the radionuclide on the probe can be achieved. Additionally the small size of the probe is advantageous especially in minimal invasive medical procedures. Preferably, the surface density of the radionuclide on the probe is from about $10^{10}$ to about $10^{13}$ atoms/cm$^2$.

In still an alternative embodiment, the radionuclide can also be collected by separating a sufficiently energetic beam of the radionuclide (e.g., a beam of Ra-223 or a beam of Ra-224) and directing the radionuclide beam onto the probe or positioning the probe in the path of the radionuclide beam, so as to allow implanting the radionuclide in the surface of the probe. Radionuclide beams can be obtained, for example, using any of the aforementioned isotope separators.

Irrespective of the method used to collect the radionuclide on or beneath the surface of the probe, the probe is preferably coated by a protective coat, which may be, for example, a thin (e.g., a few nanometers in thickness, say 5 nanometers) layer of Titanium. The protective coat serves for minimizing loss of radionuclide from the probe when the probe is in physical contact with the body. The protective coat is preferably selected so as not to prevent emission of decay chain nuclei and alpha particles from the surface of the probe.

It is expected that during the life of this patent many relevant radiotherapy devices will be developed and the scope of the term radiotherapy devices is intended to include all such new technologies a priori.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Example 1

Electrostatic Embedment of Radionuclide on a Needle

The following is a description of a typical experiment in which $^{224}$Ra atoms were electrostatically collected on a needle.

A 0.45 mm diameter nickel-plated stainless steel needle was held at a distance of about 1 cm from a 1 microCurie surface source of Th-228. The desorption probability of Ra-224 from the Th-228 was about 10%. Prior to electrostatic collection, the needle was cleaned in acetone in an ultrasonic bath for 20 minutes.

The experimental setup is shown in FIGS. 2a-c. FIG. 2a shows the Th-228 surface source. FIG. 2b is a top-view of the Th-228 source mounted inside an electrostatic collection chamber. FIG. 2c shows the needle mounted on a vertical electrode positioned in front of the Th-228 source. The potential difference between the needle and the Th-228 source was 1000 V, and the electrostatic collection chamber was filled with air at atmospheric pressure.

The Th-228 decayed by alpha emission into ionized atoms of Ra-224 having sufficient kinetic energy to be emitted into the air. Due to atomic collisions between the Ra-224 atoms and the air molecules, the kinetic energy was rapidly decreased, resulting in drifting of the Ra-224 atoms along the electric field lines in the direction of the tip of the needle. Upon impinging the needle, the Ra-224 atoms absorbed electrons from the nickel and remained on the surface thereof. The duration of the experiment was 10 days, resulting in an accumulated Ra-224 activity of about 40 nanoCurie.

The needle was subsequently coated with a layer of about 50 Å of titanium by sputtering. Once coated, the alpha particles spectrum of the needle was measured using a standard solid state detector. A desorption probability of about 15% was measured for $^{220}$Rn atoms recoiling from the coated surface.

To verify the stability of the coated needle, a few cycles of 1 minute rinsing in deionized water followed by 1 minute wash in dry $N_2$ were performed. The activity seemed to stabilize on 60% of its initial value under a plurality of such cycles.

Example 2

Preparation of a U-232

In this example, a U-232 surface source was prepared from an acidic solution containing minute amounts of a uranium salt. The U-232 surface source can be used, for example, for the purpose of preparing a surface source of Th-228, e.g., the Th-228 surface source used in Example 1.

The primary material is a 2M hydrochloric acid containing uranyl chloride at an activity density of 1 microCurie per microliter. The active material itself had an activity of 0.5 curie per gram, corresponding to an active to stable material ratio of about 1:40. The mixing of uranyl chloride with pure 2M hydrochloric acid, provided lower concentrations of active material.

A layer of about 200 nanometers of high purity (99.999%) nickel was evaporated on a 2.5×2.5 cm$^2$ polished wafer of silicon. It is to be understood that the use of the above materials is not to be considered as limiting and that other materials or compositions can be used. For example, the nickel can be replaced by any other slightly soluble metal, such as, but not limited to, molybdenum and palladium. The silicon had a thin layer of native oxide, of about 2 nanometers. Although the rate of reaction between the acid and the nickel is typically small, the wafer was cooled to a temperature of a few degrees centigrade, so as to further decrease the reaction rate.

Once cooled, an aliquot of about 1 microliter of the acid was deposited on the nickel surface, and immediately spread, substantially evenly, on about 80% of the wafer's surface area.

During the entire spreading action a flow of dry air was applied to the surface to accelerate the process of acid removal and to minimize interaction between the acid and the nickel. The deposited liquid was easily and substantially uniformly spread over the surface area, resulting in a thin layer of nickel chloride admixed with the uranyl chloride. The thickness of the layer was sufficiently small to allow a sizable fraction of nuclei resulting from alpha decay to recoil out of the surface. Note that the amount of solid material in the solution was negligible compared to the nickel chloride layer, even for the primary solution in its undiluted form (corresponding to an average thickness of less than 1 nanometer).

To test the desorption probability from the U-232 source, the following series of measurements was taken.

The source was placed in vacuum in close proximity to a collector surface while preventing physical contact therebetween. Recoils from the source were collected by collector surface for about 50 hours and the alpha particle spectra of both source and collector were measured. A high statistical accuracy of a few percents was established. The desorption probability was then determined from the measured alpha particle spectra of parent nucleus (Th-228) on the source and of daughter nucleus (Ra-224) on the collector. Due to the short duration of collection it was impractical to accurately measure alpha particle spectrum of Th-228 on the collector (resulting from the decay of U-232 on the source). The activity distribution of the source and the collector surface was further measured using a Fuji Imaging Plate™, for time exposures of 10 minutes for the source and 57 minutes for the collector.

FIGS. 3a-b show the measurements of the Fuji Plate™, where FIG. 3a show the activity distribution of the collector, and FIG. 3b show the activity distribution of the source. As show, uniform activity distributions were obtained both for the collector and the source.

The measured desorption probability for the most dilute solution tested (about 7.5 nanocuries per microliter) was about 35%. This result is to be compared with the (theoretical) maximal desorption probability, at zero depth deposition, which is 50%. For high density solution (1 microcurie per microliter) a desorption probability of about 25% was obtained.

Example 3

An Experiment on Mice Having a LAPC4 Prostate Tumor

Following is a description of an experiment on two mice having human LAPC4 prostate tumors. The objective of the experiment was to assess the transport ranges of short-lived alpha-emitting atoms released by the radiotherapy device inside a living tumor.

Materials and Methods

The radiotherapy device used in all parts of the experiment was a nickel-clad needle having Ra-224 atoms adsorbed on the surface of its tip. The preparation of the radiotherapy device was according to the description of Example 1, with exposure time of 69 hours to a 1.2 microCurie source of Th-228, resulting in needle activity of about 50 nanoCurie. In this experiment, the needle was not coated after the exposure.

The Ra-224 atoms on the needle disintegrated by alpha decay (half-life of 3.7 d) and release into the environment short-lived atoms: Rn-220 (half-life of 56 s), Po-216 (half-life of 0.15 s) and Pb-212 (half-life of 10.6 h). The short-lived atoms dispersed in the immediate surrounding of the radiotherapy device by both convection via body fluids and thermal diffusion, and disintegrated by alpha decay. The size and the shape of the irradiated region depend on the specific trajectories of the short-lived atoms prior to their decay.

The radiation emitted from the radiotherapy device and its short-lived decay products was measured using a Fuji Imaging Plate™. The photostimulable phosphor of the imaging plate records both beta decay electrons, whose range in the tissue is of the order of a few millimeters, and alpha-particles, whose range is a few dozen microns. The Ra-224 decay chain contains two beta-decays. Thus, when an imaging detecting probe made of photostimulable phosphor, is inserted into the tumor, the effective detection volume for beta radiation is significantly larger than the effective detection volume of alpha radiation.

Due to the short range of the alpha particles, detection thereof indicates the exact location of the decaying nuclei. Therefore, the primary interest in this experiment was to separate reading of alpha radiation from background beta radiation. The separation was based on the differences in the ranges of alpha- and beta-particles inside the active part of the imaging material. More specifically, imprints made by alpha particles were typically in the form of localized hot-spots spanning over 1-2 pixels (the area of each pixel is abut 200× 200 $\mu m^2$), whereas imprints made by beta decay electrons were "smeared" over many pixels and were of lower intensity. This distinction is particularly relevant to alpha particles arriving at the imaging material from its immediate surrounding, and is generally applicable when the total radiation intensity is low.

The experiment included four in vivo measurements, in which a source and detection detecting probes were inserted into the tumor for a few minutes. In addition, the experiment included a prolonged stage, in which the source was kept inside the tumor of the living mouse for 3 days. The analysis of the prolonged stage was made ex vivo.

In vivo Measurements:

Four short-duration measurements were performed on the first mouse. For each measurement, a different imaging detecting probe was used.

FIGS. 4a-d are schematic illustration of the detecting probes used in this experiment, respectively referred to herein as detecting probe 1-detecting probe 4. Specifically, detecting probe 1 had a triangular shape, about 3 millimeters in width, detecting probe 2 had a triangular shape, about 2 millimeters in width, detecting probe 3 had an arrow-like elongated pentagonal shape, about 3 millimeters in width and detecting probe 4 had a needle-like shape, about 0.7 millimeters in width.

Table 1, below summarizes the procedures employed by each detecting probe.

TABLE 1

| Probe No. | Organ | Measurement Time | Insertion Procedure |
|---|---|---|---|
| 1 | tumor | 10 minutes | Inserted prior to the insertion of the needle. The needle's axis was approximately in the detecting probe's plane and at a right angle thereto. The tip of the detecting probe and the needle were in physical contact. |
| 2 | tumor | 17 minutes | Inserted 3 minutes after the retraction of detecting probe 1 without moving the needle, approximately in the plane formed by the needle and detecting probe 1, 180° relative to the needle. The tip of the |

TABLE 1-continued

| Probe No. | Organ | Measurement Time | Insertion Procedure |
|---|---|---|---|
| 3 | tumor | 6 minutes | detecting probe was 0.5-1 mm spaced apart from the needle. Inserted immediately after the retraction of the needle (5 minutes after the retraction of detecting probe 2), at 90° to the needle. The insertion trajectory crossed the point at which the needle's tip had been and continued 3-4 mm inwards. |
| 4 | testicle (healthy) | 20 minutes | The detecting probe was inserted prior to the needle, about 2 mm into the testicle. The needle was inserted at 120° to the detecting probe, such that the distance between the tip of the detecting probe and the tip of the needle was about 2 mm. |

In all cases the detecting probe was retracted backwards along its axis, rinsed in HBSS solution, dried out, attached to a thin stainless steel plate and placed in a light-sealed box. Subsequently, the detecting probes were scanned by a stimulating beam of light, using a scanning device.

Ex vivo Measurements:

A second mouse served for a single experiment. The needle used in the above experiments on the first mouse, was inserted into the second mouse's tumor, and was trimmed so that only its tip area remained in the tumor. The skin was sewed over the tip of the needle and the source was kept inside the living mouse for 3 days. The tumor was subsequently removed and sliced into 7 slices.

Figure 5:
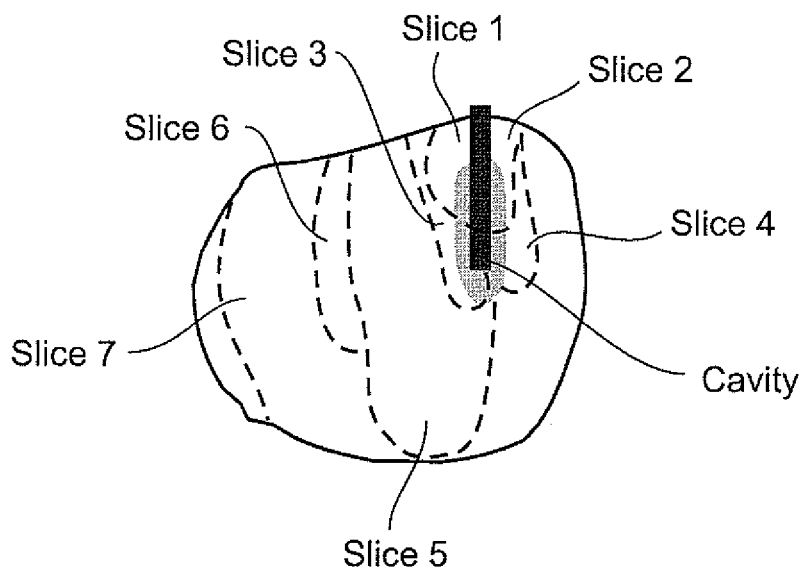
FIG. 5 is a schematic illustration of slices made on a tumor in an ex vivo experiment on mice having a LAPC4 prostate tumor, according to a preferred embodiment of the present invention.

FIG. 5 is a schematic illustration of the 7 slices, enumerated 1-7, of the removed tumor. Slices 1-4 were cut using the same scalpel. The boundary between slices 5 and 6, the boundary between slices 6 and 7, and the back side of slice 7 were cut with a clean scalpel. Also shown in FIG. 5 is a blood-filled cavity, observed in the vicinity of the needle when the tumor was dissected.

Table 2, below, summarize the dimensions and location of slices 1-7. The numerical values are approximated to ±10%.

TABLE 2

| Slice | Area [mm$^2$] | Thickness [mm] | Distance from Needle |
|---|---|---|---|
| 1 | 5 × 6 | 1 mm | 1-2 mm |
| 2 | 4 × 5 | 1-2 mm | 1-2 mm |
| 3 | 3 × 2 | 1 mm | 1 mm |
| 4 | 3 × 3 | 1 mm | 1 mm, facing slice 3 on the other side of the needle |
| 5 | 15 × 10 | 3 mm | 2-3 mm, behind slice 3 |
| 6 | 6 × 4 | 1 mm | 5-6 mm, behind slice 5 |
| 7 | 8 × 14 | 3-4 mm | 6-7 mm, behind slice 6 |

The slices were placed on the phosphoimaging plate in a manner such that the sides closer to the needle were faced upward. Each slice was covered by a piece of the phosphoimaging plate. The phosphoimaging plate and the slices were kept in ice to maintain a temperature of about 0° C. The scanning device was used for taking two measurements, 2 hours and 13 hours from the covering of the slices. The bottom plate recorded the activity of the slices for 23 hours.

Slices 1, 2, 3, 4 and 6 were dislocated by about 2-3 mm during the 2 hour measurement. No dislocation occurred during the 13 hours measurement.

Results

In vivo Measurements

Figures 6A, 6B:
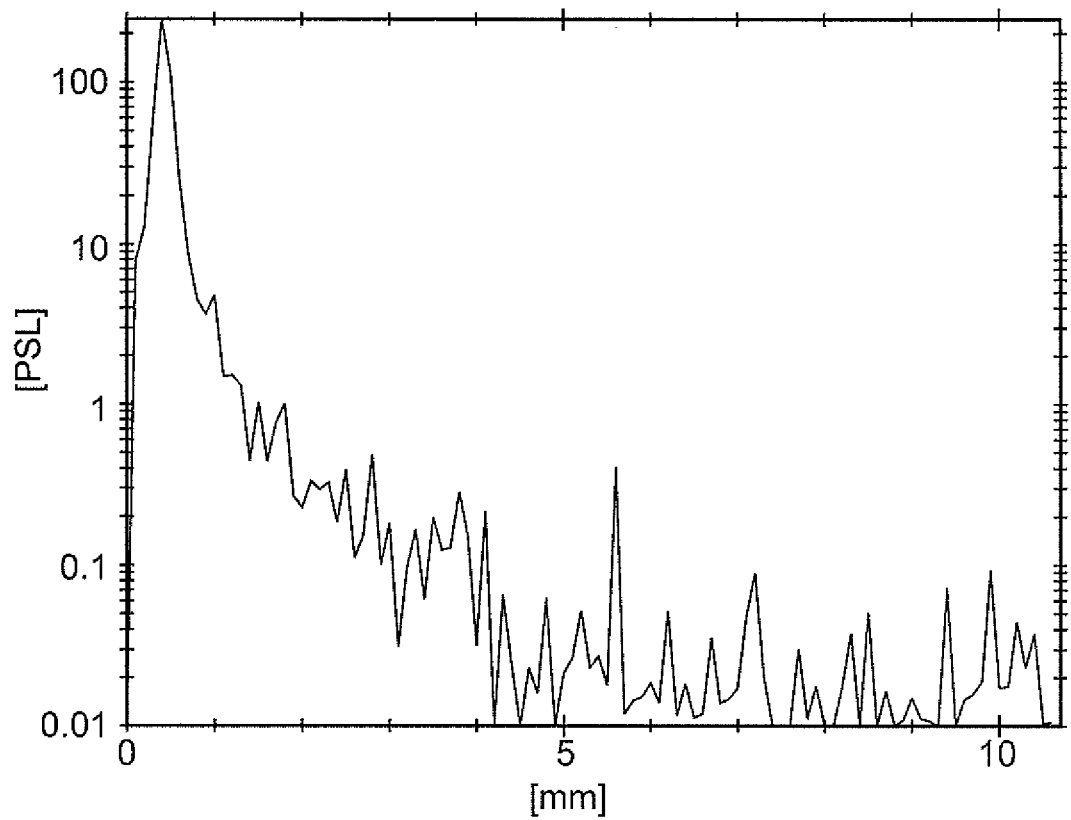

Reference is now to FIGS. 6a-b showing an image (FIG. 6a) recorded by detecting probe 1 and a corresponding radiation graph (FIG. 6b). The measured signal is shown in FIG. 6b on a logarithmic scale, as a function of the radial distance from detecting probe 1. As shown in FIGS. 6a-b, due to the physical contact between detecting probe 1 and the needle, an enhanced signal centered at the contact point was observed. Referring to FIG. 6b, the maximal signal (about 0.5 mm from the contact point) is about three orders of magnitude larger than the signal at the peripherals. The enhanced signal was surrounded by a radially decaying "halo," about 3 mm in radius, which is a consequence of the optics of the scanning device, and does not represent a real radiation pattern. In addition, to the radially decaying "halo," an axially decaying pattern was observed along detecting probe 1, about 5 mm in length, beginning at the contact point, primarily resulting from beta decay. Alpha particles imprints were inconclusive on the axially decaying pattern.

Figures 7A, 7B:
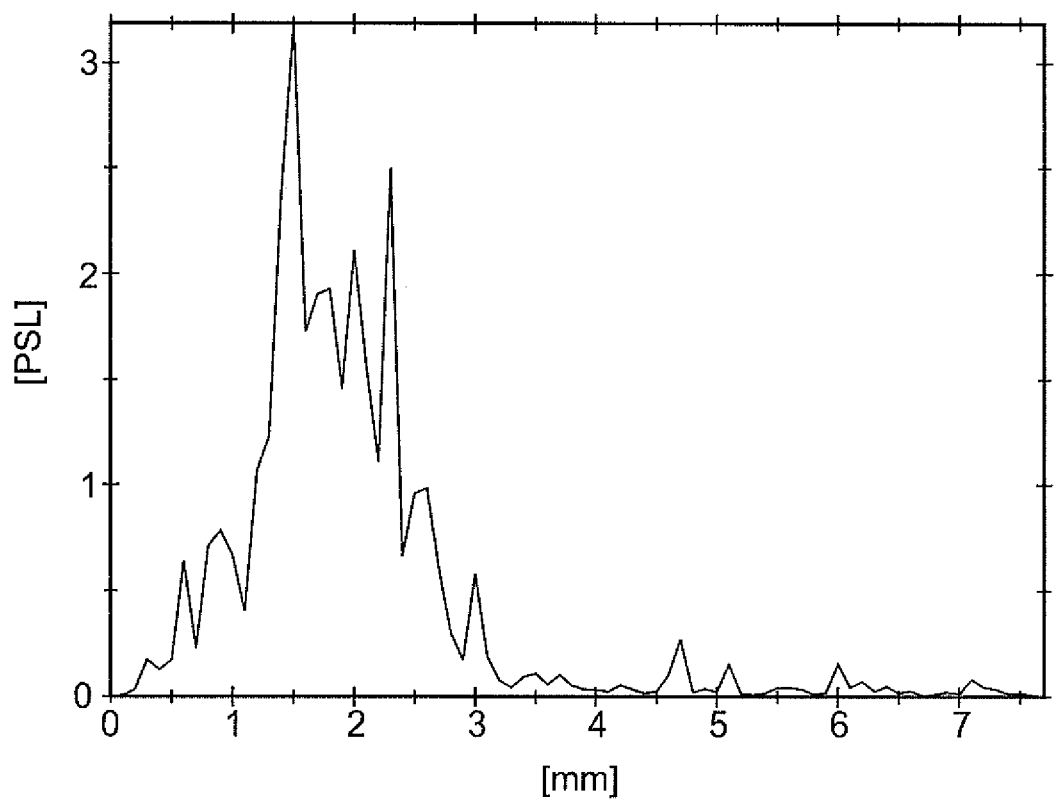

FIGS. 7a-b show an image (FIG. 7a) recorded by detecting probe 2 and a corresponding radiation graph (FIG. 7b). Due to the lack of physical contact between detecting probe 2 and the needle, the maximal signal is significantly smaller then the maximal signal in detecting probe 1 (about 35 times smaller, see FIGS. 6b and 7b). The geometrical shape of detecting probe 2 (see FIG. 4b) resulted in appearance of the maximal signal at a distance of about 1.5 mm from the needle. Similarly to detecting probe 1, the measured pattern falls off with the distance, up to about 4-5 mm from the needle.

Figure 8A:
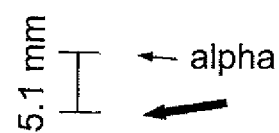
FIG. 8a is an image recorded by the detecting probe of FIG. 4c.
Figure 8B:
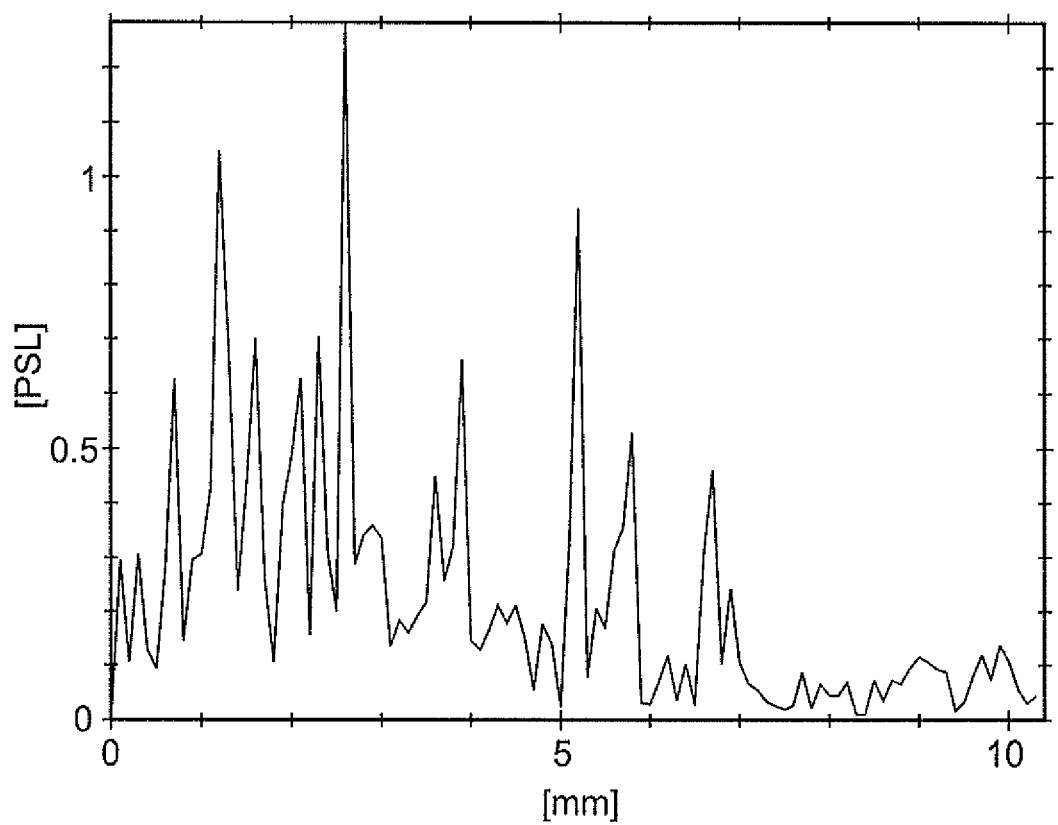

FIGS. 8a-b show an image (FIG. 8a) recorded by detecting probe 3 and a corresponding radiation graph (FIG. 8b). As stated, detecting probe 3 was inserted immediately after the retraction of the needle. This was done so as not to record electrons emitted by the needle, thereby to focus on radiation emitted by the Rn-220 atoms. As shown in FIG. 8a, the path of detecting probe 3 crossed the insertion point of the needle (designated by an arrow in FIG. 8a) and continued about 3-4 mm inward. Referring to FIG. 8b, the radiation intensity was relatively weak having a number of isolated peaks corresponding to alpha particles. A representative example of an imprint of a single alpha particle is designated by the word "alpha" in FIG. 8a. Similarly to detecting probes 1 and 2, the radiation intensity falls off with the distance from the location of the needle, up to about 5 mm from. The farthest peak was observed 5.1 mm from the insertion point.

The radiation intensity recorded by detecting probe 4, used, as stated, in a healthy testicle, was too weak to be analyzed.

Ex vivo Measurements:

FIG. 9 shows radiation patterns recorded of slices 1-7, and a clean reference plate, designated "ref." The strongest signal was recorded of slice 4, where a dark spot, about 1-2 mm in diameter and a peripheral halo, about 3-4 mm in diameter, were observed. A relatively strong signal was recorded of slice 3, about 6-7 mm in diameter. A clear, although somewhat weaker, signal was recorded of slice 5, about 2-3 mm from the needle. A very weak, but statistically valid, signal was recorded of slice 6, about 5-6 mm from the needle. No signal was recorded of slice 7.

The bottom imaging plate recorded a weak signal on the back side of slice 5, about 5-6 mm from the needle. This finding is less significant than the weak signal found on slice 6, because it may be the result of electrons arriving from the bulk of slice 5.

Discussion

A rough measurement of the needle's activity showed a drop from about 60,000 to about 20,000 counts per minute after its retraction from the tumor. Such a drop is explained by the removal of the Ra atoms of the needle, which, as stated was not coated in this experiment. The residual activity of the needle came primarily from Pb-212 atoms adsorbed on the needle during its preparation, meaning that the Ra-224 population on the needle dropped by a factor substantially larger than 3. As a result of the removal of Ra-224 from the needle, the majority of the Ra-224 atoms remained in the first mouse, and the radiation patterns recorded in the long-duration ex vivo experiment on the second mouse were weaker.

In spite of the massive Ra-224 removal in the first mouse, the insertion of the same needle into the tumor of the second mouse resulted in a 2-3 mm cavity around the insertion point. Such formation is consistent cell destruction by radiation, although simple "mechanical" damage caused by the insertion itself is yet not excluded. The weak signal recorded of slice 6 in the ex vivo experiment, indicates transport of alpha-emitting atoms to a range of about 5-6 mm from the needle. The imprints of alpha particles recorded by detecting probe 3, about 5 mm from the needle, can also be considered as evidence of such migration.

Example 4

An Experiment on Mice Having a B-16 Melanoma

Following is a description of an experiment on two mice belonging to the C57B1/6 inbred, treated with B-16 melanoma cells (approximately 100,000 cells at 0.1 ml of HBSS buffer per mouse). The radiotherapy was implemented 16 days after inoculation of the tumors, at which point the tumors sized 19.5 mm, for a first mouse, and 17.2 mm for a second mouse.

Materials and Methods

Two nominally identical radioactive sources were prepared (one for each mouse). Each source consisted of a 0.45 mm diameter nickel-plated stainless steel needle, recoil implanted in vacuum with Ra-224. After the vacuum implantation, both needles were rinsed in deionized water and washed in a stream of dry $N_2$, in order to minimize the release of Ra atoms from the surface after insertion. The $^{224}$Ra activity upon insertion was approximately 1-2 nanoCurie in each case.

The Ra-224 atoms on the needle disintegrated by alpha decay as further detailed hereinabove (see, e.g., Example 3).

The needles were inserted subcutaneously to a depth of about 5 mm into each tumor, and were externally trimmed thereafter. The mice were kept alive for two days after insertion, at which point the tumors were removed and dissected manually at measured distances from the source (beginning at the periphery towards the insertion point and using a different scalpel for each dissection to avoid cross contamination). A series of samples, each about 1 mm³ in volume, were taken from the dissected parts, 5 from the first mouse, and 4 from the second mouse. Each sample was flattened between a glass microscope slide and a 7 μm Mylar® foil, covering a surface of about 2-4 cm².

All samples were placed on a Fuji™ plate, using the Mylar® foil for physical separation between the samples and the plate. Three consecutive measurements were taken. A first measurement started at t=0 for a duration of ΔT=5 hours, a second measurement started at t=6.75 hours for a duration of ΔT=17.1 hours and a third measurement started at t=25 hours for a duration of ΔT=5 hours.

Results

A clear signal appeared in all three measurements in samples taken 2 mm and 11 mm from the source in the first mouse, and 0.5 mm, 6 mm and 15 mm from the source in the second mouse. The time dependence of the measured intensity correlated with the half life of Ra-224 (3.66 d). No discernible signal was detected on the other samples.

FIGS. 10*a-f* exemplify images (FIGS. 10*a*, 10*c* and 10*e*) and corresponding radiation graphs (FIGS. 10*b*, 10 *d* and 10*f*, respectively) of the three consecutive measurements taken about 11 mm from the needle of the first mouse. FIGS. 10*a-b* correspond to the first measurement, FIGS. 10*c-d* correspond to the second measurement and FIGS. 10*e-f* correspond to the third measurement. As shown in FIGS. 10*a-f*, the intensity of the signals decreases with time.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A radiotherapy method, comprising:
   positioning at least one removable radiotherapy device having a surface and a predetermined amount of a radionuclide retainably embedded on or beneath said surface in proximity to and/or within a tumor of a subject, for a predetermined time period, said predetermined amount and said predetermined time period selected sufficient for said radionuclide to administer a predetermined therapeutic dose of decay chain nuclei and alpha particles into said tumor;

wherein said radionuclide is selected from the group consisting of Radium-223 and Radium-224, and wherein said embedding ensures that said radionuclide remains in said at least one radiotherapy device while said decay chain nuclei and alpha particles are recoiled outside said surface.

2. The method of claim 1, further comprising removing said radionuclide of said tumor once said predetermined therapeutic dose of decay chain nuclei and alpha particles is administered.

3. The method of claim 1, wherein said at least one radiotherapy device comprises a needle.

4. The method of claim 1, wherein said at least one radiotherapy device comprises at least one bead.

5. The method of claim 1. wherein said radionuclide is soluble in a solute and further wherein said positioning said radionuclide comprises administering to the subject in proximity to and/or within said tumor a solution of said radionuclide in said solute.

6. The method of claim 1, further comprising recording a dose of said alpha particles.

7. The method of claim 1, wherein said predetermined therapeutic dose of said decay chain nuclei and said alpha particles is from about 100 to about 100000 rem.

8. The method of claim 1, wherein said predetermined amount of said radionuclide is from about 10 nanoCurie to about 10 microCurie.

9. The method of claim 1, wherein said predetermined time is from about 10 seconds to about 10 hours.

10. The method of claim 1, wherein said predetermined time is a few days.

11. A method of removing a tumor and remnants thereof present in a body of a subject, the method comprising:
  (a) debulking at least a portion of the tumor and exposing tissue surrounding the tumor; and
  (b) positioning at least one removable radiotherapy device having a surface and a predetermined amount of a radionuclide retainably embedded on, or beneath said surface in proximity to and/or within said surrounding tissue, for a predetermined time period, said predetermined amount and said predetermined time period selected sufficient for said radionuclide to administer a predetermined therapeutic dose of decay chain nuclei and alpha particles into said surrounding tissue, wherein said radionuclide is selected from the group consisting of Radium-223 and Radium-224, and wherein said embedding ensures that said radionuclide remains in said at least one radiotherapy device while said decay chain nuclei and alpha particles are recoiled outside said surface.

12. The method of claim 11, wherein said debulking is performed laparoscopically.

13. The method of claim 11, wherein said debulking is performed endoscopically.

14. The method of claim 11, wherein said debulking is performed surgically.

15. The method of claim 11, wherein said debulking is performed ablatively.

16. The method of claim 11, wherein said debulking is by a laser beam.

17. The method of claim 15, wherein said debulking comprises applying heat to the tumor.

18. The method of claim 15, wherein said debulking is by a microwave antenna.

19. The method of claim 15, wherein said debulking is by a radiofrequency electrode.

20. The method of claim 15, wherein said debulking is by an ultrasound device.

21. The method of claim 11, wherein said positioning of said radionuclide is by a radiotherapy device having a surface whereby said radionuclide is on or beneath said surface.

22. The method of claim 21, wherein said radiotherapy device comprises a needle.

23. The method of claim 11 further comprising recording a dose of said alpha particles.

24. The method of claim 11, wherein said predetermined therapeutic dose of said decay chain nuclei and said alpha particles is from about 100 to about 100000 rem.

25. The method of claim 11, wherein said predetermined amount of said radionuclide is from about 10 nanoCurie to about 10 microCurie.

26. The method of claim 11, wherein said predetermined time is from about 10 seconds to about 10 hours.

27. The method of claim 11, wherein said predetermined time is a few days.

* * * * *